United States Patent [19]

Glasscock

[11] 4,105,579

[45] Aug. 8, 1978

[54] PROCESS FOR PRODUCING PHARMACEUTICAL GRADE ALUMINUM HYDROXIDE GELS

[75] Inventor: Green Bateman Glasscock, Lewes, Del.

[73] Assignee: Barcroft Company, Lewes, Del.

[21] Appl. No.: 663,652

[22] Filed: Mar. 4, 1976

[51] Int. Cl.$^2$ ............................................. B01J 13/00
[52] U.S. Cl. ................................... 252/317; 423/629; 424/156; 424/157
[58] Field of Search ................ 252/317; 424/156, 157; 423/629

[56] References Cited

U.S. PATENT DOCUMENTS

| | | | |
|---|---|---|---|
| 3,055,737 | 9/1962 | Wilson, Jr. et al. | 252/317 X |
| 3,066,012 | 11/1962 | Wilson, Jr. et al. | 252/317 X |
| 3,099,524 | 7/1963 | Grossmith | 424/156 X |
| 3,239,416 | 3/1966 | Rubino | 424/156 X |
| 3,577,533 | 5/1971 | Rider | 424/156 X |

*Primary Examiner*—Richard D. Lovering
*Attorney, Agent, or Firm*—James A. Nicholson; Raymond Underwood

[57] ABSTRACT

A process for producing aluminum hydroxide gels substantially free of sodium ions involves a heterogeneous reaction between an aqueous solution of a water soluble aluminum salt and an aqueous slurry of a water soluble alkaline earth carbonate.

5 Claims, No Drawings

PROCESS FOR PRODUCING PHARMACEUTICAL GRADE ALUMINUM HYDROXIDE GELS

This invention relates to a process for producing aluminum hydroxide gels of pharmaceutical grade and particularly a gel product which is free of or substantially free of sodium salts.

Physicians are becoming increasingly aware of the fact that sodium salts are counterindicated for persons having hypertension and other cardio-vascular diseases and for persons having renal impairment. For instance, such persons are instructed to eliminate or severely curtail their consumption of table salt. If such persons have gastrointestinal disorders which are medicinally benefited by antacids, including aluminum hydroxide gel, it is quite important that the gel not be contaminated by entrained sodium ions. A process which produces aluminum hydroxide gel with no appreciable sodium ion content, at a relatively low cost, is desirable.

Prior processes for producing aluminum hydroxide gel have not been entirely satisfactory either because the process produced a gel product which included an undesirably large amount of sodium salts or because the process was too complex and expensive to be commercially practicable. According to one prior process, aluminum chloride is reacted with sodium carbonate but this has required extensive flushing with wash water to remove the sodium chloride. Another known process involves reacting sodium aluminate with gaseous carbon dioxide but this also involves using considerable wash water to reduce the sodium ion content to an acceptable level.

The U.S. Pat. No. 3,066,012 to C. P. Wilson, Jr. et al is of interest because it involves as a first step the reaction of an aluminum sulfate solution with calcium carbonate to form a basic aluminum sulfate sol, the second step of isolating the sol, the third step of adding a sodium carbonate solution to form the alumina gel and the fourth step of washing out the sodium salts and other soluble impurities. This process involves a series of homogeneous step-wise reactions. The commercial processes mentioned earlier above likewise involve homogeneous reactions.

The process of the present invention involves a heterogeneous reaction in water between a water soluble aluminum salt such as aluminum chloride and an alkaline earth carbonate such as calcium carbonate. These reactants should be selected or be properly purified to minimize sodium, iron and other contaminants. The process can be carried out either as a batch or as a continuous operation. A definite advantage of the chemical reaction is that it may occur at ambient atmospheric pressure and temperature. In either a batch or a continuous process reaction should be allowed to continue for at least from 5 to 20 minutes.

Aluminum chloride is the preferred aluminum salt reactant and it should constitute from 14 to 28% by weight of the solution which is used. Calcium carbonate is the preferred carbonate reactant and it should constitute from 4 to 10% by weight of the aqueous slurry which is used. These two aqueous preparations are combined in a relative amount so that the reaction bath is maintained between about pH4.7 and 5.5. This will generally require the addition to 100 grams of calcium carbonate of from 70 to 90 grams of aluminum chloride but it is preferred that the reaction conditions be controlled on the basis of the pH of the reaction.

The exact nature of the heterogeneous reaction is not fully understood but it would appear that the fixing of the carbonate by the solid calcium carbonate insures that carbonate is present at the site of precipitation. This gives the aluminum ion the immediate opportunity of complexing with the carbonate, which results in the most reactive and stable gel. This stabilizing reaction is evidenced by a split of the carbonate band in the 1400 – 1500 $cm^{-1}$ region of the infrared spectrum.

The precipitated aluminum hydroxide gel is isolated from the reaction bath and then washed to obtain it in a purified form. A unique feature of this process is that the gel product which it produces is considerably more reactive than gels produced by present day commercial processes. Because of its exceptional acid consuming capacity it is particularly valuable as a medicinal antacid.

Instead of aluminum chloride, other water soluble aluminum salts may be substituted, such as the sulfate or the nitrate, an amount being used to yield the same aluminum content. Instead of calcium carbonate, other water insoluble alkaline earth carbonates may be substituted, such as magnesium carbonate an amount being used to yield the same carbonate ion content.

In a batch operation it is preferable, but not essential, to add the aluminum salt in its water solution, to a reactor vessel containing the alkaline earth carbonate in its aqueous slurry. The vessel should be equipped with a stirrer or other mechanical agitator and the aluminum salt solution should gradually be added to it. Representative examples are the following:

EXAMPLE 1

A total of 5000 ml. of water was charged to an agitated reactor under ambient conditions and 210 gm. of U.S.P. calcium carbonate was added and dispersed, thus forming a slurry. Aluminum chloride solution (28% by weight) was then fed to the slurry at a rate of 15 ml./min. until a total of 490 ml. solution had been fed. The reaction bath assayed generally a pH 5.0 – 5.5 at the end of this addition. The resulting aluminum hydroxide gel was isolated as by filtration and given several water washes.

The 4% aluminum hydroxide gel suspension which was prepared from the gel slurry exhibited the following properties:

| | |
|---|---|
| Assay, % $Al_2O_3$ | 8.53 |
| pH | 6.70 |
| Viscosity, cps | 1488 |
| Acid consumption, ml. | |
| 0.1 N HCl/gm. | 25.2 |
| CaO, % | 0.44 |
| Chlorides, % | 0.04 |

EXAMPLE 2

In Example 1, magnesium carbonate was substituted for the calcium carbonate and the product assayed as follows:

| | |
|---|---|
| Assay, % $Al_2O_3$ | 6.98 |
| pH | 7.10 |
| Viscosity, cps | 1084 |
| Acid consumption, ml. | |
| 0.1 N HCl/gm. | 25.2 |
| $Mg(OH)_2$, % | 0.38 |
| $Cl^-$, % | — |

EXAMPLE 3

In Example 1, aluminum sulfate was substituted for the aluminum chloride.

EXAMPLE 4

This illustrates a continuous process in which the reactants are constantly being added and intermixed with each other and the resulting product is isolated.

A calcium carbonate slurry, maintained at a consistency to contain 5% $CaCO_3$ by weight, and an aluminum chloride solution, maintained at a consistency to contain 14% by weight $AlCl_3$, were fed simultaneously to an agitated reactor at ambient pressure and temperature. The calcium carbonate feed rate was about 1 gal/min and the aluminum chloride feed was maintained by a pH controller-reactor system to give a reactor pH around 5.0. Overflow from the reactor, containing the aluminum hydroxide gel slurry, was filtered and washed on a rotary filter.

The 4% aluminum hydroxide gel suspension prepared from this particular reaction showed the following properties:

| | |
|---|---|
| Assay, % $Al_2O_3$ | 8.09 |
| pH | 6.50 |
| Viscosity, cps | 420 |
| Acid consumption, ml. 0.1 N HCl/gm | 26.2 |
| CaO, % | 0.86 |
| Chlorides, % | 0.15 |

EXAMPLE 5

In Example 4, magnesium carbonate was substituted for the calcium carbonate and the product assayed as follows:

| | |
|---|---|
| Assay, % $Al_2O_3$ | 7.59 |
| pH | 7.10 |
| Viscosity, cps | 1358 |
| Acid consumption, ml. 0.1 N HCl/gm | 24.7 |
| $Mg(OH)_2$, % | 0.44 |
| $Cl^-$, % | — |

EXAMPLE 6

In any of the above examples the relative amounts of the reactants can be varied within the limits of this invention.

The foregoing examples are to be construed as illustrations of this invention and are not considered to be limitations thereof.

I claim:

1. A process for producing aluminum hydroxide gels which comprises combining water, a water soluble salt of aluminum selected from the group consisting of aluminum chloride, aluminum sulfate and aluminum nitrate, and a water insoluble alkaline earth carbonate under heterogeneous reaction conditions while maintaining a reaction pH between 4.7 and 5.5 and isolating the aluminum hydroxide gel.

2. The process of claim 1 in which a constantly flowing stream of an aqueous solution of the aluminum salt is continuously added to a constantly flowing aqueous slurry of the carbonate.

3. The process of claim 1 in which the carbonate is selected from the group consisting of calcium and magnesium carbonates.

4. An aluminum hydroxide gel produced by carrying out the process of claim 1.

5. A process for producing aluminum hydroxide gels which comprises adding a 14 – 28% by weight aqueous solution of an aluminum salt selected from its chloride, aluminum sulfate and aluminum nitrate to a 4 – 10% by weight aqueous slurry of a carbonate selected from the group consisting of calcium and magnesium carbonate under agitated, heterogeneous reaction conditions while maintaining a reaction pH between 4.7 and 5.5 by adjustment of the relative amounts of the reactants, and isolating the aluminum hydroxide gel.

* * * * *